US012727774B2

(12) United States Patent
Leahy et al.

(10) Patent No.: US 12,727,774 B2
(45) Date of Patent: Sep. 8, 2026

(54) INLINE FLUIDIC MEASUREMENT SYSTEM

(71) Applicant: Analog Devices International Unlimited Company, Limerick (IE)

(72) Inventors: Claire E. Leahy, Listowel (IE); Youri Victorovitch Ponomarev, Rotselaar (BE)

(73) Assignee: Analog Devices International Unlimited Company (IE)

( * ) Notice: Subject to any disclaimer, the term of this patent is extended or adjusted under 35 U.S.C. 154(b) by 222 days.

(21) Appl. No.: 18/369,745

(22) Filed: Sep. 18, 2023

(65) Prior Publication Data

US 2025/0090037 A1 Mar. 20, 2025

(51) Int. Cl.
*A61B 5/026* (2006.01)

(52) U.S. Cl.
CPC ...... *A61B 5/026* (2013.01); *A61B 2560/0228* (2013.01)

(58) Field of Classification Search
CPC ........... A61B 5/026; A61B 2560/0228; A61B 5/1495; A61M 2205/33; A61M 2205/70; A61M 2205/702
See application file for complete search history.

(56) References Cited

U.S. PATENT DOCUMENTS

| | | | |
|---|---|---|---|
| 4,734,184 | A | 3/1988 | Burleigh et al. |
| 2010/0094114 | A1 | 4/2010 | Robinson et al. |
| 2022/0291165 | A1 | 9/2022 | Bolognia et al. |
| 2023/0149608 | A1 | 5/2023 | Ponomarev et al. |

FOREIGN PATENT DOCUMENTS

| | | | | |
|---|---|---|---|---|
| GB | 2512842 A | * 10/2014 | | A61B 5/1495 |
| JP | 2005-501227 | 1/2005 | | |
| JP | 2018-534578 | 7/2020 | | |
| WO | WO 2002/097415 | 12/2002 | | |
| WO | WO 2024/100260 A1 | 5/2024 | | |

OTHER PUBLICATIONS

Extended European Search Report for EP Application No. 24199344.3 dated Nov. 18, 2024 in 16 pages.

* cited by examiner

*Primary Examiner* — Stephen D Meier
*Assistant Examiner* — Quang X Nguyen
(74) *Attorney, Agent, or Firm* — Knobbe, Martens, Olson & Bear, LLP

(57) ABSTRACT

A fluid sensor system and method of operating the fluid sensor system is disclosure herein. A fluid sensor device of the fluid sensor system can be connected with a treatment system in-line. The fluid sensor system may receive a second solution different from a first calibration fluid to use as a calibration fluid to reduce costs associated with storing calibration fluid inside the fluid sensor device prior to use with the treatment system.

16 Claims, 5 Drawing Sheets

INLINE FLUIDIC MEASUREMENT SYSTEM

TECHNICAL FIELD

The present application relates to an in-line fluid sensor system. More particularly, the in-line fluid sensor system can use an external calibration fluid source.

BACKGROUND

An in-line fluid sensor system can be used during many treatment procedures to measure and/or monitor a property of a sample fluid, for example, a patient's blood. Calibration fluids are often used in such a fluid sensor system to calibrate sensors of the system before and/or after each measurement of the sample fluid to allow prolonged use of sensors with sufficient accuracy. The operational lifetime of the fluid sensor system is often determined by the amount of calibration fluid available and the number of calibration sequences that can be performed. Storing and maintaining a large volume of calibration fluid can be costly due to the larger footprint and more expensive storage solution.

SUMMARY

The disclosure relates generally to an in-line fluid sensor system.

An aspect is directed to a method of calibrating a fluid sensor device connected in-line with a treatment system. The method includes providing a first calibration fluid stored in a calibration compartment to a sensing element, taking a first measurement of the first calibration fluid with the sensing element, providing a second calibration fluid from a second calibration fluid source, taking a second measurement of the second calibration fluid with the sensing element, and calibrating the sensing element using the second calibration fluid.

A variation of the aspect above further includes connecting an inlet of the fluid sensor device with a first point of a treatment line of the treatment system, and an outlet of the fluid sensor device with a second point of the treatment line of the treatment system.

A variation of the aspect above further includes storing the second calibration fluid in a second calibration compartment.

A variation of the aspect above is, wherein the second calibration compartment is empty before being connected to the treatment system.

A variation of the aspect above further includes determining a difference between the first measurement of the first calibration fluid and the second measurement of the second calibration fluid.

A variation of the aspect above is, wherein calibrating the sensing element comprising comparing a measurement of the second calibration with the difference between the first measurement of the first calibration fluid and the second measurement of the second calibration fluid.

A variation of the aspect above is, wherein the treatment line connects a patient and the second calibration fluid source.

A variation of the aspect above is, wherein the second calibration fluid source is external to the fluid sensor device.

A variation of the aspect above is, wherein the second calibration fluid comprises a physiological solution.

A variation of the aspect above further includes providing a sample fluid from the patient through the treatment line to the sensing element.

A variation of the aspect above further includes after providing the sample fluid from the patient through the treatment line to the sensing element, controlling a flow direction of fluid in the treatment line to provide the second calibration fluid from the treatment solution source to the sensing element.

Another aspect of this disclosure is directed to a fluid sensor system configured to take measurements of a sample fluid in-line with a treatment system. The fluid sensor system includes a fluid sensor device. The fluid sensor device includes a sensing channel configured to receive a sample fluid from the treatment system, a first calibration compartment containing a first calibration fluid and in fluidic communication with the sensing channel, a second calibration compartment configured to receive a second calibration fluid from a second calibration fluid source, and a sensing element configured to interact with and transduce a property of a fluid in the sensing channel. The second calibration compartment is in fluidic communication with the sensing channel.

A variation of the aspect above is, wherein the first calibration compartment has a volume in a range of 5-100 micro litre.

A variation of the aspect above is, wherein the second calibration fluid source is external to the fluid sensor system.

A variation of the aspect above is, wherein the second calibration fluid source comprises a treatment line of the treatment system.

A variation of the aspect above is, wherein the second calibration fluid is a physiological fluid.

A variation of the aspect above further includes a processor configured to determine a difference between a first measurement taken by the sensing element of the first calibration fluid and a second measurement taken by the sensing element of the second calibration fluid, and calibrate the sensing element based at least on a measurement taken by the sensing element of the second calibration fluid and the determined difference.

A variation of the aspect above is, wherein the second calibration compartment is empty during a storage mode, during which the fluid sensor system is not connected to the treatment system.

Another aspect of this disclosure is directed to a fluid sensor system configured to take measurements of a sample fluid in-line with a treatment system. The fluid sensor system includes a fluid sensor device. The fluid sensor device includes a sensing channel configured to receive a sample fluid from the treatment system, a calibration compartment containing a first calibration fluid and in fluidic communication with the sensing channel, and a sensing element configured to interact with fluid in the sensing channel. The calibration compartment has a volume in a range of 5-100 micro litre.

A variation of the aspect above further includes a controller configured to control one or more valves to selectively direct only a second calibration fluid from the treatment system to the sensing channel in a calibration mode, and to control the one or more valves to selectively direct only the sample fluid from the treatment system to the sensing channel in a sensing mode.

A variation of the aspect above further includes a processor configured to determine a difference between a first measurement taken by the sensing element of the first calibration fluid and a second measurement taken by the sensing element of the second calibration fluid, and calibrate the sensing element based at least on a measurement taken by the sensing element of the second calibration fluid and the determined difference in the calibration mode.

BRIEF DESCRIPTION OF THE DRAWINGS

The present disclosure is described with reference to the accompanying drawings, in which like reference characters reference like elements, and wherein.

DETAILED DESCRIPTION

Generally described, one or more aspects of the present disclosure relate to an in-line fluid sensor system. An in-line fluid sensor system can be connected to, for example, a treatment line of a treatment system and function without disruption of the treatment. In certain embodiments, this disclosure relates to systems and methods of taking measurements of a sample fluid using multiple calibration fluid sources. In some embodiments, the fluid sensor system can include an empty fluid compartment configured to receive and store a physiological fluid from a treatment line to use as a calibration fluid when the fluid sensor system is connected to a treatment system. In some embodiments, the fluid sensor system can be configured to receive a physiological solution directly from the treatment line and use as a calibration fluid when the fluid sensor system is connected to a treatment system without storing the physiological solution in a dedicated calibration fluid compartment of the fluid sensor system. In other embodiments, the fluid sensor system can store a solution in a second calibration fluid compartment in additional to a first calibration fluid compartment storing a calibration fluid.

Figure 1:
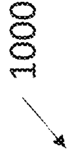
FIG. 1 is a schematic system diagram of a fluid sensor system.
Figure 1:
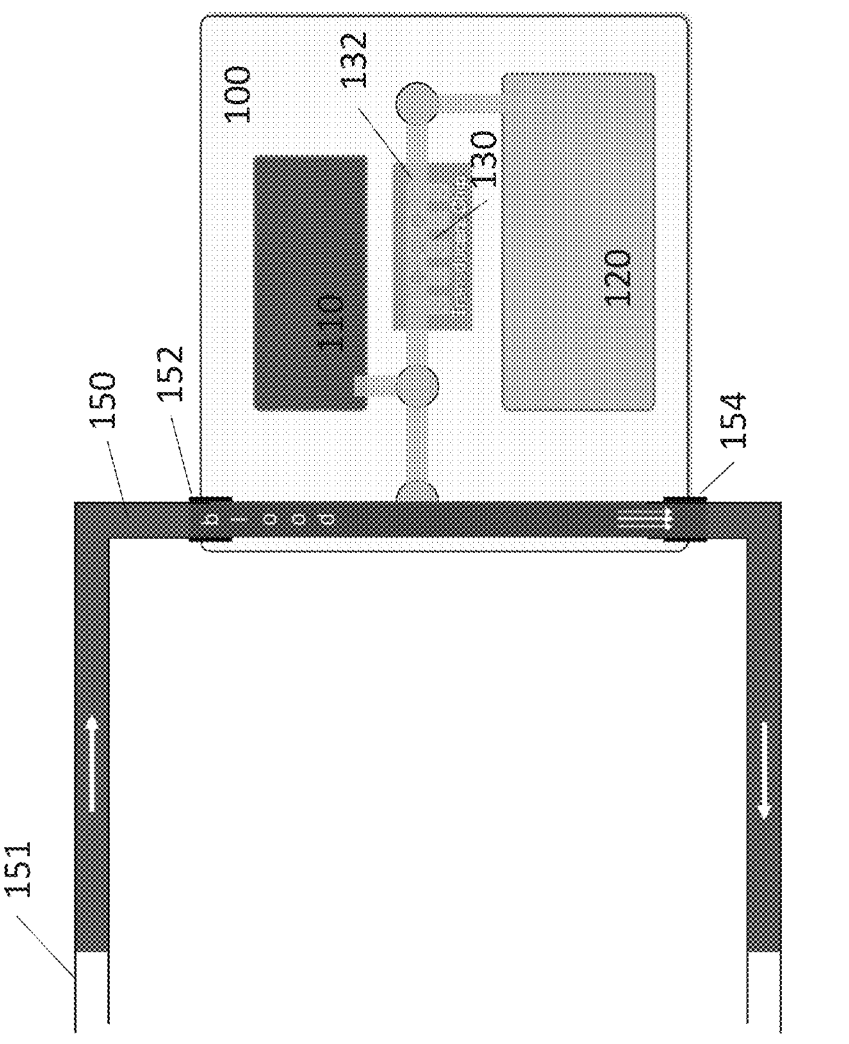

As shown in FIG. 1, a fluid sensor system 1000 can include a fluid sensor device 100 comprising a sensing element 130 including a plurality of functionalized transducers or electrodes that, when exposed to a sample fluid, can measure a property or constituent component of the sample fluid (e.g., a patient's blood) and transmit a signal indicative of the property or constituent component of the sample fluid (e.g., a concentration of the a particular constituent component of the sample fluid). During a treatment procedure, the fluid sensor device 100 can be connected in-line to a treatment line 150 of a treatment system and be configured to operate in a plurality of modes. For example, during a sensing mode, a sample fluid 150 can enter the fluid sensor device 100 through an inlet 152 and exit the fluid sensor device 100 through an outlet 154. After the sample fluid 150 entered the fluid sensor device 100, the treatment line 150 may be directed to a sensing channel 132 to interact with the sensing element 130 and allow the sensing element 130 to take measurements.

During a calibration mode, the sample fluid 150 can be directed to bypass the electrodes of the sensing element 130 to pass directly from the inlet 152 to the outlet 154 without entering the sensing channel 132. Instead, a calibration fluid (e.g., a biocompatible fluid such as water, saline, etc.) of a certain volume can be provided from a calibration compartment 110 of the fluid sensor device 100 to the sensing element 130. The calibration fluid can serve to reset the fluid sensor device 100 by presenting a known property (e.g., a voltage representative of a certain concentration of a component) that the sensing element 130 can measure and calibrate against. For example, in some embodiments, the calibration fluid can have a known potassium level, and the sensing element 130 may measure a voltage of the calibration fluid representative of concentration of potassium in the calibration fluid. In some embodiments, the sensing element 130 may be calibrated based on an offset between a measured voltage of the calibration fluid and a stored voltage value stored in memory. Additionally, the calibration fluid can improve accuracy of the sensing element 130 by flushing the sensing channel 132 to remove residual sample fluid and/or other debris. In some embodiments, at the end of the calibration mode, the calibration fluid can exit the sensing channel 132 and enter a waste compartment 120 to be store therein. Further details regarding how the fluid sensor device 100 may operate (e.g., take measurements, store information, and transmit signals) can be found in U.S. patent application Ser. No. 18/055,799 (published as US 2023/0149608 A1), the entire disclosure of which is incorporated by reference as if fully set forth herein.

Figure 2:
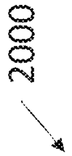
FIG. 2 is a schematic system diagram of a fluid sensor system according to an embodiment of the present disclosure.
Figure 2:
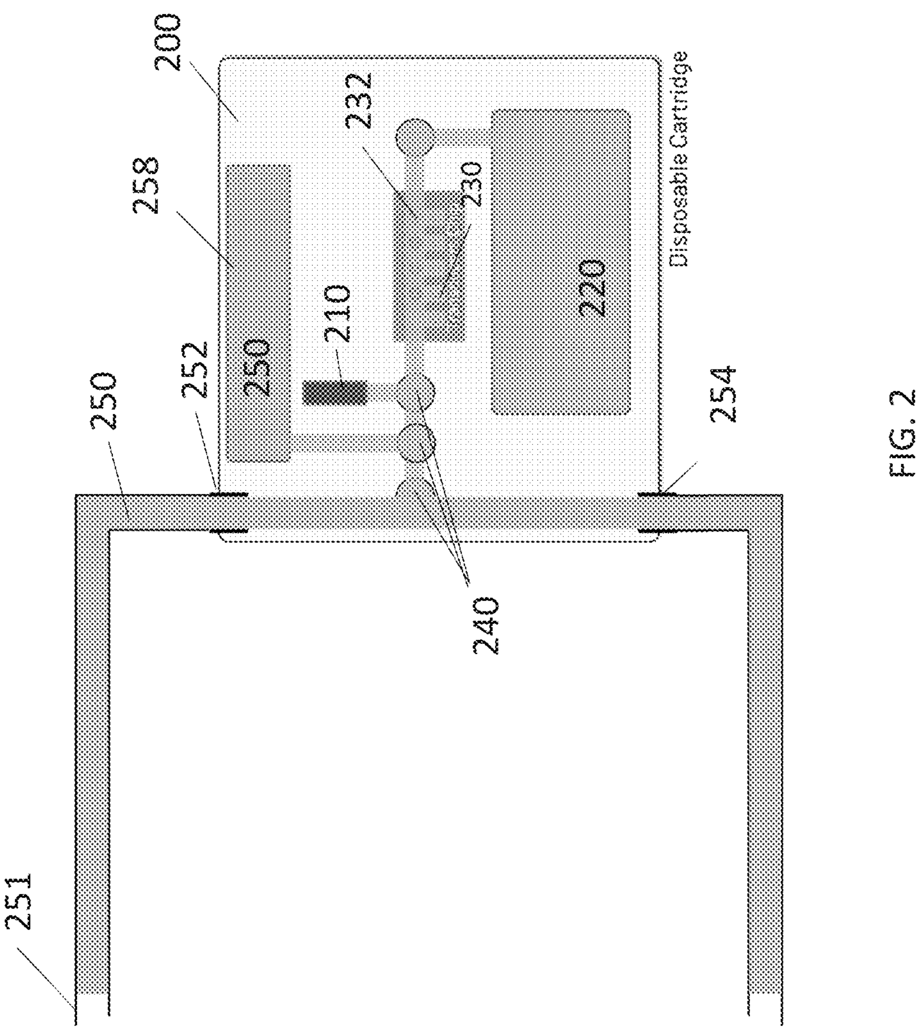
Figures 3A, 3B, 3C:
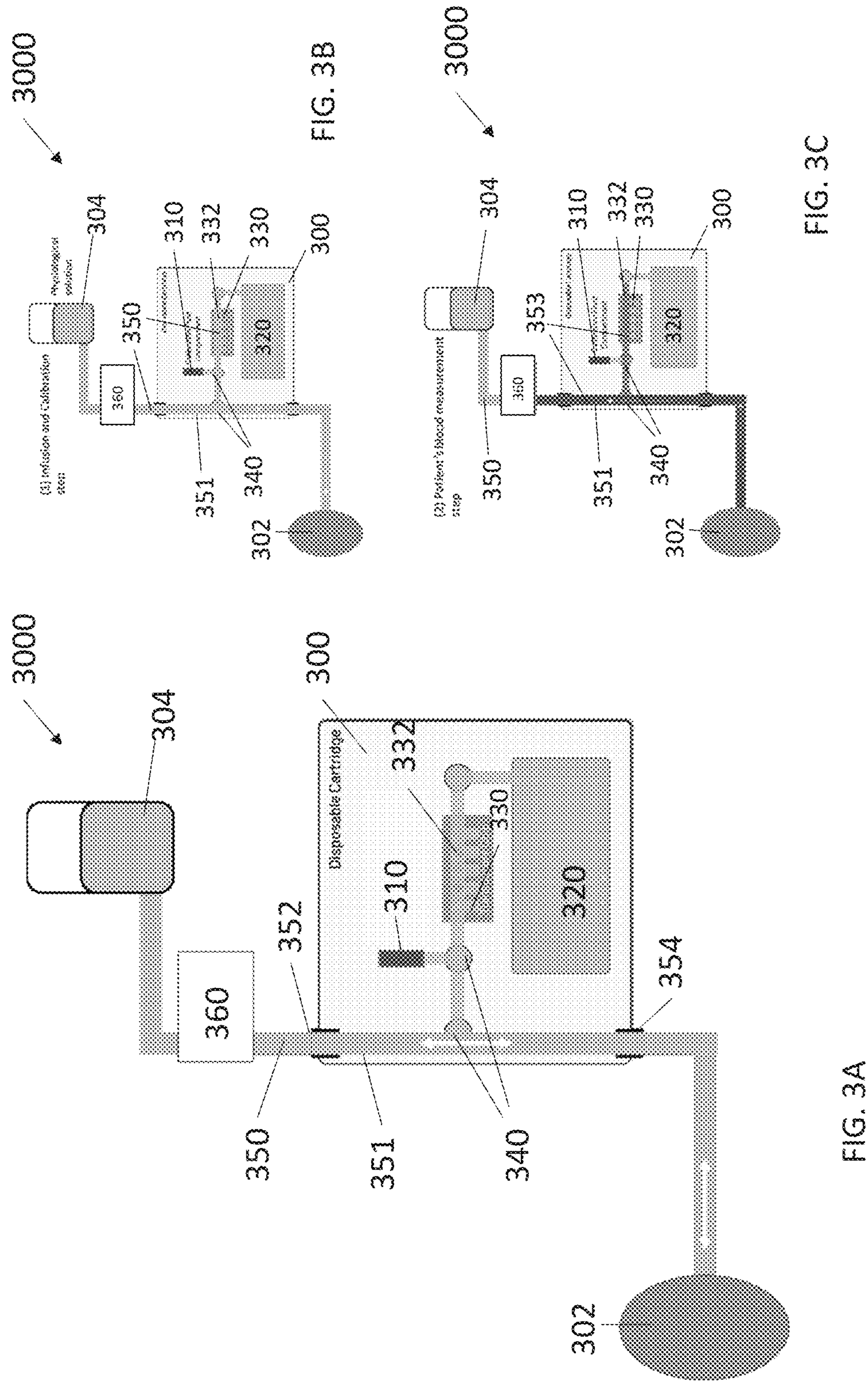
FIG. 3A is a schematic system diagram of a fluid sensor system according to another embodiment of the present disclosure.
FIG. 3B is a schematic system diagram of the fluid sensor system of FIG. 3A during a calibration mode.
FIG. 3C is a schematic system diagram of the fluid sensor system of FIG. 3A during a sample fluid sensing mode.

As shown in FIG. 1, the fluid sensor device 100 can include a large calibration fluid compartment 110 storing an amount of calibration fluid that can last the entire operational lifetime of the fluid sensor device 100. For example, the amount of calibration fluid stored in the calibration fluid compartment 110 may be enough to calibrate a sensing element 130 before and/or after each measurement of a sample fluid for as many testing or sample cycles as the fluid sensor device 100 is designed for. To ensure that the calibration fluid is fresh and has a constant property to calibrate the sensing element 130, keeping a large volume of calibration fluid inside the fluid sensor device 100 can be costly and inconvenient, and can increase the overall size of the device 100. In accordance with various embodiments disclosure herein, FIGS. 2-3C shows embodiments of fluid sensor systems that can utilize multiple calibration fluid sources and allow a reduced-size calibration compartment to be filled during storage and transportation, prior to a treatment procedure. Unless otherwise noted, the components of the fluid sensor system 2000 may be the same as or generally similar to like-numbered components of the fluid sensor system 1000 with the reference numerals incremented by 100 relative to the reference numerals of FIG. 1, and may function or operate in a generally similar manner.

Figure 4:
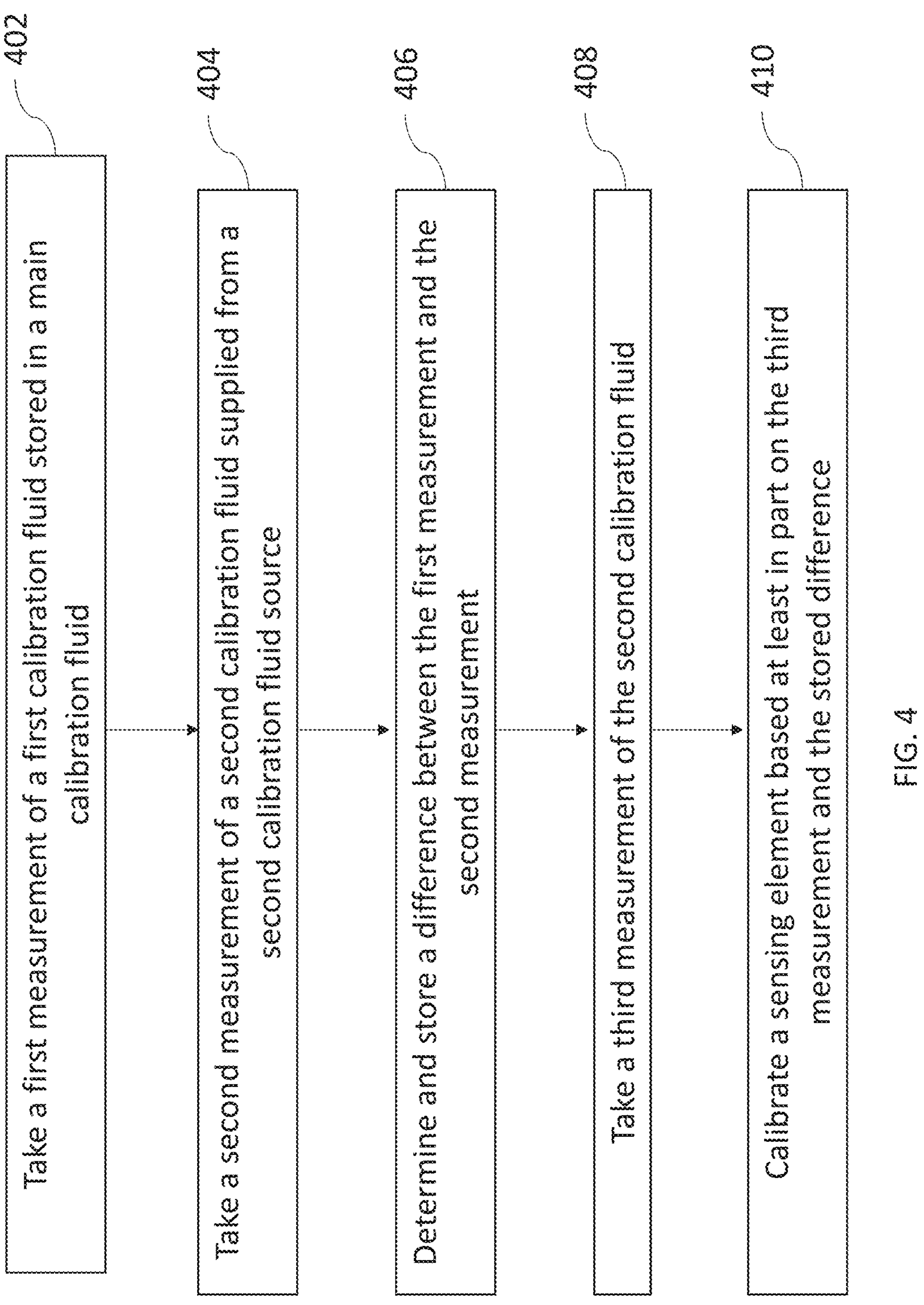
FIG. 4 is a flowchart showing an exemplary method of operating a fluid sensor system according to the present disclosure.
Figure 5:
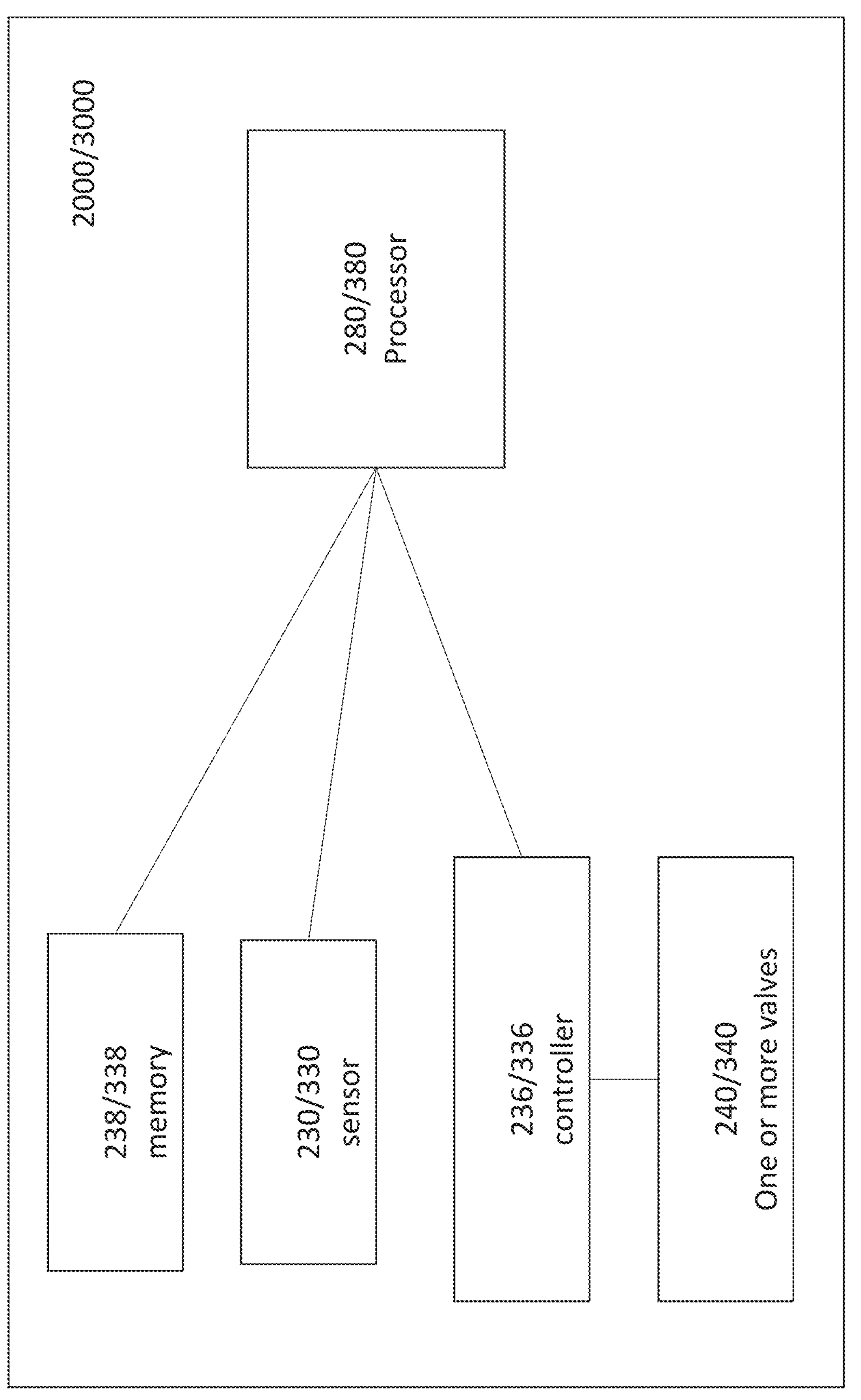
FIG. 5 is a block diagram showing electrical components in the fluid sensor system of FIG. 2 or FIG. 3A.

A fluid sensor system 2000 disclosed herein can include a fluid sensor device 200 as shown in FIG. 2 and be operated according to the flowchart in FIG. 4. The fluid sensor device 200 can similarly include a sensing element 230 configured to interact with fluid inside the sensing channel 232. In some embodiments, the sensing element 230 can take measurements of the fluid inside the sensing channel 232 and transmit a signal indicative of the measurements, e.g., a voltage relative to a reference electrode. In some embodiments, with reference to FIG. 5, the fluid sensor system 2000 can include a processor 280 and/or a memory 238 configured to process and/or store information transmitted from the sensing element 230. In some embodiments, the fluid sensor system 2000 can also include a controller 236 configured to control the fluid sensor device 200 to operate in a plurality of modes (e.g., a calibration mode, a sensing mode, and etc.). In some embodiments, the controller 236 can be configured to control one or more valves 240 on the fluid sensor device 200 to direct flow of fluid inside the fluid sensor device 200. In some embodiments, the controller 236, the processor 280 and/or the memory 238 may be positioned on the fluid sensor device 300. In some embodiments, the controller 236, the processor 280 and/or the memory 238 may be positioned on a separate reader device, connectable to the fluid sensor device 200. In some embodiments, the controller 236 and processor 280 may be formed or provided in the same chip or device, or in separate chips or devices.

In some embodiments, the fluid sensor device 200 can include a calibration compartment 210 that is filled with a calibration fluid before the fluid sensor device 200 is connected with a treatment system. In some embodiments, the calibration compartment 210 can have a volume that is less than the total volume of a calibration fluid required for the entire operational lifetime of the fluid sensor device 200. In some embodiments, the calibration compartment 210 can have a volume, e.g., in the range of 5-100 micro litre, in the range of 10-50 micro litre, in the range of 10-100 micro liter, in the range of 20-40 micro litre, in the range of 100 to 1000 micro liter, or about 30 micro litre.

In some embodiments, the fluid sensor device 200 can include a second calibration fluid compartment 258 that is empty before the fluid sensor device 200 is connected with a treatment system. In some embodiments, the second calibration fluid compartment 258 can be kept empty in storage or during transportation to reduce costs. In other embodiments, the second calibration fluid compartment 258 may be at least partially pre-filled with a fluid in storage and/or during transportation. In some embodiments, the fluid sensor device 200 can be connected in-line with a treatment line 251 to be connected with the treatment system. In some embodiments, only a second calibration fluid 250 (e.g., a physiological solution) may run through the treatment line 251. In some embodiments, the second calibration fluid 250 and/or a sample fluid (e.g., a patient's blood) may selectively run through the treatment line 251.

In some embodiments, when the fluid sensor device 200 is first connected with a treatment system, the controller 236 of the fluid sensor device 200 can be configured to initiate a first calibration mode wherein the controller 236 may cause a calibration fluid inside the calibration compartment 210 to enter the sensing channel 232 and interact with the sensing element 230. In some embodiments, the controller 236 may control the one or more valves 240 to provide the calibration fluid to flow from the calibration compartment 210 to the sensing channel 232. During the first calibration mode, or block 402 as illustrated in FIG. 4, the sensing element 230 can take a first measurement of the calibration fluid from calibration compartment 210 and transmit a signal (e.g., a potential difference between the electrodes of the sensing element 230 and a reference electrode) including the first measurement to the memory 230 of the fluid sensor system 2000 for storage and/or processing by the processor 280 (see FIG. 5).

In some embodiments, after the calibration fluid from calibration compartment 210 interacts with the sensing element 230 and passes down to a waste compartment 220, the controller 236 of the fluid sensor device 200 can then cause the second calibration fluid 250 (e.g., a physiological solution) from the treatment line 251 entering through an inlet 252 of the fluid sensor device 200 to enter the second calibration fluid compartment 258. Thereafter, in some embodiments, the controller 236 can cause the second calibration fluid 250 to be stored inside the second calibration fluid compartment 258. In some embodiments, the controller 236 can cause the second calibration fluid 250 to enter the second calibration fluid compartment 258 and stored therein by controlling the one or more valves 240.

In some embodiments, a second calibration mode can then be initiated by the controller 236 to provide the second calibration fluid 250 from the second calibration fluid compartment 258 to the sensing channel 232 and interact with the sensing element 230. As shown in FIG. 4, the sensing element 230 may take a second measurement of the second calibration fluid 250 and transmit a signal (e.g., a potential difference between the electrodes of the sensing element 230 and a reference electrode) including the first measurement to the memory 230 of the fluid sensor system 2000 for storage and/or processing by the processor 280 (see FIG. 5). In some embodiments, in block 406, the processor 280 can then compare the first measurement taken in block 402 and the second measurement taken in block 404 to determine a difference to be stored in the memory 238. The stored difference can be used in subsequent calibration modes as a reference for calibrating the sensing element 230 using the treatment solution or the second calibration fluid 250 coming from an external source instead of the pre-existing calibration fluid from the calibration compartment 210. For example, in some embodiments, after a sample fluid sensing event where a sample fluid is run through the treatment line 251 to the sensing channel 232 to interact with the sensing element 230, the second calibration fluid 250 can be provided from the second calibration fluid compartment 258 to the sensing channel 232 to flush any remaining sample fluid or debris, and interact with the sensing element 230 for the sensing element 230 to take a third measurement. In some embodiments, in block 410, the sensing element 230 can then calibrate and re-set the sensing element 230 using the third measurement and the stored difference as a reference. Thereby, sufficient calibration fluid for only one calibration event (e.g., the first calibration event) can be stored in the calibration compartment 210 before the fluid sensor device 200 is connected to the treatment system.

In some embodiments, after a fluid is provided to the sensing channel 232 and interacts with the sensing element 230, the fluid flows down to the waste compartment 220. In some embodiments, one of the one or more valves 240 can be positioned between the sensing channel 232 and the waste compartment 220 such that the controller 236 can also be configured to control when and whether the fluid is to be directed to the waste compartment 220.

FIGS. 3A-3C show another embodiment of a fluid sensor system 3000 disclosed herein. The fluid sensor system 3000 can include a fluid sensor device 300 configured to be connected with a treatment system. In some embodiments, the fluid sensor system 3000 can operate similarly to the fluid sensor system 2000 as illustrated in FIG. 4. Unless otherwise noted, the components of the fluid sensor system 3000 may be the same as or generally similar to like-numbered components of the fluid sensor system 2000 with the reference numerals incremented by 100 relative to the reference numerals of FIG. 2, and may function or operate in a generally similar manner.

In some embodiments, the fluid sensor device 300 can be configured to connect to a treatment line 351 in-line, with an inlet 352 connected to one point on the treatment line 351 and an outlet 354 connect to another point on the treatment line 351. In some embodiments, one end of the treatment line 351 can connect to a second calibration fluid source 304, and the other end of the treatment line 351 can connect to a patient 302. In some embodiments, a second calibration fluid 350 (e.g., a physiological solution) and/or a sample fluid 353 (e.g., a patient's blood) may selectively run through the treatment line 351. In some embodiments, the treatment line 351 can include a pump 360 configured to control a flow of fluid(s) inside the treatment line 351. In some embodiments, the pump 360 may be configured to cause the second calibration fluid 350 to flow through at least a portion of the treatment line 351 and towards the fluid sensor device 300, or cause the sample fluid 352 to flow through at least a portion of the treatment line 351 and towards the fluid sensor device 300. When the fluid sensor device 300 is first connected to the treatment line 351, in some embodiments, a controller 336 (see FIG. 5) of the fluid sensor system 3000 may control one or more valves 340 to keep the second calibration fluid 350 in the treatment line 351 without going into the sensing channel 332 as shown in FIG. 3A.

In some embodiments, the fluid sensor device 300 can include a calibration compartment 310 that has a volume that is less than the total volume of a calibration fluid required for the entire operational lifetime of the fluid sensor device 300. In some embodiments, the calibration compartment 310 can have a volume, e.g., in the range of 5-100 micro litre, in the range of 10-50 micro litre, in the range of 20-40 micro litre, or around 30 micro litre. In some embodiments, the calibration compartment 310 can have a volume that is sufficient for only one calibration event as described above.

In some embodiments, different from the fluid sensor system 2000 of FIG. 2, the fluid sensor device 300 of the fluid sensor system 3000 may omit a second calibration compartment as compared to the embodiment of FIG. 2, and instead draw the second calibration fluid 350 directly from the treatment line 351 to a sensing channel 332 during a calibration mode/event without being stored or entering a separate compartment. During a first calibration mode, in some embodiments, the fluid sensor system 3000 can similarly provide the calibration fluid from calibration compartment 310 to the sensing channel 332 and operate according to blocks 402 to take a first measurement of the calibration fluid in the 310 with a sensing element 330 (see FIG. 4).

Thereafter, during a second calibration mode, the controller 236 may control the one or more valves 340 to direct the second calibration fluid 350 to flow to the sensing channel 332 and interact with the sensing element 330 as shown in FIG. 3B. The fluid sensor system 3000 can operate according to block 404 to take a second measurement of the second calibration fluid 350 with the sensing element 330 and determine a difference between the first measurement and the second measurement with a processor 380 (see FIG. 5). The fluid sensor system 3000 may then store the difference in a memory 338 according to block 406, and use the stored difference to calibrate the sensing element 330 during the second and/or each subsequent calibration event.

In some embodiments, the first measurement of the calibration fluid from calibration compartment 310 can also be stored in the memory 338. Thereby, in some embodiments, the fluid sensor system 3000 may instead take a measurement of the second calibration fluid 350 and determine a difference against the first measurement during each subsequent calibration events, and use the determined difference to calibrate the sensing element 330 without storing the difference.

In some embodiments, when the second calibration fluid source is changed out to supply a third solution different from the second calibration fluid 350, the processor 280 of the fluid sensor system 3000 may receive an input that the second calibration fluid source has been changed and configure the memory to erase any stored information (e.g., the stored difference) regarding the previous calibration fluid. In some embodiments, the calibration compartment 310 may include sufficient calibration fluid for conducting two or more calibration event such that a new measurement can be taken of the calibration fluid to determine a new difference.

After the initial calibration event(s), the fluid sensor system 3000 may operate to provide the sample fluid 352 by changing a flow of fluids inside the treatment line 351 using the pump 360, and provide the sample fluid 352 into the sensing channel 332 by controlling the one or more valves 340 as shown in FIG. 3C during a sensing mode. After a measurement of the sample fluid 352 has happened, the fluid sensor system 3000 may again initiate a calibration mode to flush out any remnants and re-calibrate the sensing element 330 as described above.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosed fluid sensor system. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including," "comprising," "incorporating," "consisting of," "have," "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed fairly. Moreover, such joinder references do not necessarily infer that two elements are directly connected to each other. Additionally, all numerical terms, such as, but not limited to, “first,” “second,” “third,” “primary,” “secondary,” “main” or any other ordinary and/or numerical terms, should also be taken only as identifiers, to assist the reader’s understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application.

What is claimed is:

1. A method of calibrating a fluid sensor device connected in- line with a treatment system, the method comprising:
- providing a first calibration fluid stored in a calibration compartment to a sensing element,
- taking a first measurement of the first calibration fluid with the sensing element,
- providing a second calibration fluid from a second calibration fluid source,
- taking a second measurement of the second calibration fluid with the sensing element, and
- calibrating the sensing element using the second calibration fluid, wherein calibrating the sensing element comprises comparing a subsequent measurement of the second calibration fluid with a difference between the first measurement of the first calibration fluid and the second measurement of the second calibration fluid.

2. The method of claim 1, further comprising connecting an inlet of the fluid sensor device with a first point of a treatment line of the treatment system, and an outlet of the fluid sensor device with a second point of the treatment line of the treatment system.

3. The method of claim 2, wherein the treatment line connects a patient and the second calibration fluid source.

4. The method of claim 3, further comprising providing a sample fluid from the patient through the treatment line to the sensing element.

5. The method of claim 4, further comprising after providing the sample fluid from the patient through the treatment line to the sensing element, controlling a flow direction of fluid in the treatment line to provide the second calibration fluid from the second calibration fluid source to the sensing element.

6. The method of claim 1, further comprising storing the second calibration fluid in a second calibration compartment.

7. The method of claim 6, wherein the second calibration compartment is empty before being connected to the treatment system.

8. The method of claim 1, wherein the second calibration fluid source is external to the fluid sensor device.

9. The method of claim 1, wherein the second calibration fluid comprises a physiological solution.

10. A fluid sensor system configured to take measurements of a sample fluid in-line with a treatment system, the fluid sensor system comprising:
- a fluid sensor device comprising:
  - a sensing channel configured to receive a sample fluid from the treatment system;

- a first calibration compartment containing a first calibration fluid and in fluidic communication with the sensing channel;
  - a second calibration compartment configured to receive a second calibration fluid from a second calibration fluid source, wherein the second calibration compartment is in fluidic communication with the sensing channel;
  - a sensing element configured to interact with and transduce a property of a fluid in the sensing channel; and
  - a processor configured to:
    - determine a difference between a first measurement taken by the sensing element of the first calibration fluid and a second measurement taken by the sensing element of the second calibration fluid, and
    - calibrate the sensing element based at least on subsequent measurement taken by the sensing element of the second calibration fluid and the determined difference.

11. The fluid sensor system of claim 10, wherein the first calibration compartment has a volume in a range of 5-100 microliters.

12. The fluid sensor system of claim 10, wherein the second calibration fluid source is external to the fluid sensor system.

13. The fluid sensor system of claim 12, wherein the second calibration fluid source comprises a treatment line of the treatment system.

14. The fluid sensor system of claim 10, wherein the second calibration compartment is empty during a storage mode, during which the fluid sensor system is not connected to the treatment system.

15. A fluid sensor system configured to take measurements of a sample fluid in-line with a treatment system, the fluid sensor system comprising:
- a fluid sensor device comprising:
  - a sensing channel configured to receive a sample fluid from the treatment system;
  - a calibration compartment containing a first calibration fluid and in fluidic communication with the sensing channel, wherein the calibration compartment has a volume in a range of 5-100 microliters;
  - a sensing element configured to interact with fluid in the sensing channel;
  - one or more valves configured to selectively direct a second calibration fluid from the treatment system to the sensing channel and selectively direct the sample fluid from the treatment system to the sensing channel; and
  - a processor configured to:
    - determine a difference between a first measurement taken by the sensing element of the first calibration fluid and a second measurement taken by the sensing element of the second calibration fluid, and
    - calibrate the sensing element based at least on subsequent measurement taken by the sensing element of the second calibration fluid and the determined difference.

16. The fluid sensor system of claim 15, further comprising a controller configured to control the one or more valves to selectively direct only the second calibration fluid from the treatment system to the sensing channel in a calibration mode, and to control the one or more valves to selectively direct only the sample fluid from the treatment system to the sensing channel in a sensing mode.

* * * * *